United States Patent
Liu et al.

(10) Patent No.: US 10,302,449 B2
(45) Date of Patent: May 28, 2019

(54) STEP COUNTING METHOD AND DEVICE

(71) Applicant: Goertek Inc., Weifang (CN)

(72) Inventors: Song Liu, Weifang (CN); Fupo Wang, Weifang (CN); Na Li, Weifang (CN)

(73) Assignee: GOERTEK INC., Weifang (CN)

( * ) Notice: Subject to any disclaimer, the term of this patent is extended or adjusted under 35 U.S.C. 154(b) by 93 days.

(21) Appl. No.: 14/891,581

(22) PCT Filed: Dec. 25, 2014

(86) PCT No.: PCT/CN2014/001179
§ 371 (c)(1),
(2) Date: Nov. 16, 2015

(87) PCT Pub. No.: WO2015/100707
PCT Pub. Date: Jul. 9, 2015

(65) Prior Publication Data
US 2016/0298984 A1    Oct. 13, 2016

(30) Foreign Application Priority Data
Dec. 31, 2013  (CN) .......................... 2013 1 0751226

(51) Int. Cl.
*G01C 22/00* (2006.01)
*A61B 5/11* (2006.01)
(Continued)

(52) U.S. Cl.
CPC ............ *G01C 22/006* (2013.01); *A61B 5/112* (2013.01); *A61B 5/1118* (2013.01); *A61B 5/725* (2013.01);
(Continued)

(58) Field of Classification Search
CPC ..... G01C 22/006; A61B 5/112; A61B 5/1118; A61B 5/1123; A61B 2562/0219; A63B 24/0062; A63B 2220/17
(Continued)

(56) References Cited

U.S. PATENT DOCUMENTS

| 4,791,574 A | 12/1988 | Thoone et al. |
| 5,583,776 A | 12/1996 | Levi et al. |

(Continued)

FOREIGN PATENT DOCUMENTS

| CN | 101354265 A | 1/2009 |
| CN | 102818913 A | 12/2012 |

(Continued)

OTHER PUBLICATIONS

Korean Written Opinion dated May 9, 2017, issued in connection with KR Application No. 10-2015-7031810 (English Translation).
(Continued)

*Primary Examiner* — Tha-O H Bui
(74) *Attorney, Agent, or Firm* — Troutman Sanders LLP

(57) ABSTRACT

The present invention provides a step counting method and device. The method comprises the following steps performed repeatedly: a) obtaining three monoaxial acceleration signals with a predetermined length from triaxial output of a triaxial acceleration sensor worn on a walkrunner; b) performing high-pass filtering on each obtained monoaxial acceleration signal; c) performing pitch detection on each high-pass filtered monoaxial acceleration signal; d) using the pitch obtained in each pitch detection as a cut-off frequency to set a low-pass or band-pass filter, and performing low-pass or band-pass filtering on corresponding high-pass filtered monoaxial acceleration signal by using it; e) obtaining acceleration signal extreme value points from each low-pass or band-pass filtered monoaxial acceleration signal and
(Continued)

removing interfering extreme value points therein; f) counting the number of the acceleration signal extreme value points after the interfering extreme value points have been removed; g) determining the accumulative walkrun step number of the walkrunner. The method can count steps accurately.

13 Claims, 6 Drawing Sheets

(51) Int. Cl.
    *A61B 5/00*         (2006.01)
    *A63B 24/00*       (2006.01)

(52) U.S. Cl.
    CPC ........ *A61B 5/7225* (2013.01); *A63B 24/0062* (2013.01); *A61B 2562/0219* (2013.01); *A63B 2220/17* (2013.01)

(58) Field of Classification Search
    USPC ......................................................... 702/160
    See application file for complete search history.

(56) References Cited

U.S. PATENT DOCUMENTS

| | | | |
|---|---|---|---|
| 5,908,396 A | | 6/1999 | Hayakawa et al. |
| 6,386,041 B1 | | 5/2002 | Yang |
| 2002/0107649 A1* | | 8/2002 | Takiguchi ............ A61B 5/1038 702/75 |
| 2004/0064286 A1* | | 4/2004 | Levi ...................... G01C 21/12 702/141 |
| 2006/0284979 A1 | | 12/2006 | Clarkson |
| 2007/0208544 A1 | | 9/2007 | Kulach et al. |
| 2009/0240461 A1 | | 9/2009 | Makino et al. |
| 2010/0024531 A1 | | 2/2010 | Senoo |
| 2013/0054181 A1 | | 2/2013 | Lakhzouri et al. |
| 2013/0085700 A1 | | 4/2013 | Modi et al. |
| 2013/0138394 A1 | | 5/2013 | Shiga |
| 2015/0272480 A1* | | 10/2015 | Senta ...................... G01P 15/18 600/595 |
| 2016/0058372 A1* | | 3/2016 | Raghuram ........... A61B 5/0205 600/595 |
| 2017/0102247 A1* | | 4/2017 | Rivolta ................ G01C 22/006 |

FOREIGN PATENT DOCUMENTS

| | | |
|---|---|---|
| CN | 103148864 A | 6/2013 |
| CN | 103323615 A | 9/2013 |
| CN | 103344249 A | 10/2013 |
| CN | 103727959 B | 9/2016 |
| JP | 2001143048 A | 5/2001 |
| JP | 2002197437 A | 7/2002 |
| JP | 2005049202 A | 2/2005 |
| JP | 2005157465 A | 6/2005 |
| JP | 2006127026 A | 5/2006 |
| JP | 5144128 B2 | 2/2013 |
| KR | 1020080104123 A | 1/2008 |
| KR | 1020110139143 A | 12/2011 |

OTHER PUBLICATIONS

Extended European Search Report dated May 2, 2016 issued in EP International Application No. 14876915.1.

* cited by examiner

STEP COUNTING METHOD AND DEVICE

This application is the U.S. National Phase of International Patent Application Serial No. PCT/CN2014/001179, filed on Dec. 25, 2014, which claims priority to Chinese Patent Application No. CN 201310751226.0, filed on Dec. 31, 2013, both of which applications are herein incorporated by reference in their entirety.

FIELD OF THE INVENTION

The present invention relates to the field of sports equipment, in particular, relates to a step counting method and device.

BACKGROUND OF THE INVENTION

Pedometer is a device capable of calculating the walking or running (hereinafter brief as walkrun) step number of its wearer. With more and more concern of the health condition of human beings, the pedometer becomes an aid for customizing sports schemes quantitatively, and has been widely used.

Currently, the pedometer is mainly divided into two types, mechanical pedometer and electronic pedometer. The mechanical pedometer generates electrical pulses through the vibration of internal reed or elastic ball of the pedometer caused by its wearer's walkrun, and counts the number of these electrical pulses through an internal processor, thus implementing the function of step counting. The cost of mechanical pedometer is relatively low, but the accuracy and sensitivity are poorer. The electronic pedometer is generally based on the output signal of an acceleration sensor to obtain its wearer's walkrun step number. The electronic pedometer is low in power consumption, and both its accuracy and sensitivity are superior to the mechanical pedometer. Therefore, the electronic pedometer becomes a hotspot in the current study of pedometer.

Human walkrun is a process with quasi-periodicity, therefore, although the accelerations generated in each direction during human walkrun are different, they all have the same quasi-periodicity, which is reflected by that the accelerations in different directions contain the same pitch. The pedometer based on acceleration sensor can produce an oscillatory acceleration signal during its wearer's walkrun and analyze the acceleration signal, to obtain the walkrun step number of its wearer. Specifically, the current pedometer based on acceleration sensor determines its wearer's walkrun step number according to the number of peaks of oscillatory acceleration signal it produces. The disadvantage of the step counting methods of these pedometers is in that the direct use of peaks of oscillatory acceleration signal to determine the walkrun step number can cause poor step counting accuracy, which will affect the implementation of sports scheme of the pedometer's wearer.

SUMMARY OF THE INVENTION

The present invention is made for solving the problem existing in the aforesaid prior art. One object is for providing a step counting method and device, and the step counting method and device can count walkrun step number of the pedometer's wearer more accurately.

For achieving the aforesaid object, in one aspect of the present invention, a step counting method is provided, comprising the following steps performed repeatedly:

a) obtaining three monoaxial acceleration signals with a predetermined length from triaxial output of a triaxial acceleration sensor worn on a walkrunner;
b) performing high-pass filtering on each obtained monoaxial acceleration signal;
c) performing pitch detection on each high-pass filtered monoaxial acceleration signal, to obtain the pitch of each monoaxial acceleration signal;
d) selecting the lowest pitch in the three monoaxial acceleration signals as a cut-off frequency to set a low-pass or band-pass filter, and performing low-pass or band-pass filtering on each high-pass filtered monoaxial acceleration signal by using the low-pass or band-pass filter;
e) obtaining acceleration signal extreme value points from each low-pass or band-pass filtered monoaxial acceleration signal and removing interfering extreme value points therein;
f) counting the number of the acceleration signal extreme value points of each low-pass or band-pass filtered monoaxial acceleration signal after the interfering extreme value points have been removed;
g) determining the walkrun step number obtained from this round of step counting based on the number of the acceleration signal extreme value points in three monoaxial acceleration signals with the interfering extreme value points removed as counted in step f), and calculating the accumulative walkrun step number of the walkrunner.

One or more methods of autocorrelation function method, cepstrum method, linear predictive coding method, and average magnitude difference function method can be used in the pitch detection. Preferably, performing pitch detection on the high-pass filtered monoaxial acceleration signal can comprise:

c2) calculating the autocorrelation function $\rho(\tau)$ of each high-pass filtered monoaxial acceleration signal by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, a(n) is the n-th value of each high-pass filtered monoaxial acceleration signal, N is the predetermined length of the signal, and 0≤n<N, $\tau$ is a delay time, $\rho(\tau)$ is a normalized autocorrelation function of the signal;

c3) obtaining the value of $\tau$ corresponding to the maximal value of $\rho(\tau)$, and the reciprocal of the $\tau$ value is the pitch of the signal.

Further preferably, before obtaining the autocorrelation function $\rho(\tau)$ of each high-pass filtered monoaxial acceleration signal, the method can further comprise: c1) performing attenuation process on the signal by using a filter with which the attenuation of signal energy increases progressively from low frequency to high frequency.

Wherein, the removing the interfering extreme value points from the acceleration signal extreme value points comprises: filtering out the interfering extreme value points from the acceleration signal extreme value points through time gap; or, filtering out the interfering extreme value points from the acceleration signal extreme value points through time gap and magnitude value.

Preferably, the interfering extreme value points may comprise such an acceleration signal extreme value point that the time gap between the acceleration signal extreme value point and the previous acceleration signal extreme value point is smaller than a predetermined threshold. Or, the interfering extreme value points may comprise acceleration signal extreme value points, whose magnitude values are not maximal, among each group of acceleration signal extreme value points in which the time gap between any two adjacent acceleration signal extreme value points is smaller than a predetermined threshold.

Preferably, the step g) can comprise:
if the energy of each monoaxial acceleration signal not being markedly different, averaging the number of the acceleration signal extreme value points, with the interfering extreme value points removed, corresponding to each axis, and taking the average number as the walkrun step number obtained in this round of step counting;
or, if the energy of each monoaxial acceleration signal being markedly different, determining the walkrun step number obtained in this round of step counting based on the number of the acceleration signal extreme value points, with the interfering extreme value points removed, corresponding to the monoaxial acceleration signal with the largest energy.

Preferably, the step counting method can further comprise: calculating displacement based on quadratic integral of at least one monoaxial acceleration signal for time.

According to another aspect of the present invention, a step counting device is provided, comprising:
a triaxial acceleration sensor;
a monoaxial acceleration signal obtaining unit, for obtaining three monoaxial acceleration signals with a predetermined length from the triaxial output of the triaxial acceleration sensor worn on a walkrunner;
a high-pass filtering unit, for performing high-pass filtering on each monoaxial acceleration signal obtained from the monoaxial acceleration signal obtaining unit;
a pitch detecting unit, for performing pitch detection on each high-pass filtered monoaxial acceleration signal to obtain the pitch of each monoaxial acceleration signal;
a low-pass or band-pass filtering unit, for selecting the lowest pitch in the three monoaxial acceleration signals as a cut-off frequency to set a low-pass or band-pass filter, and performing low-pass or band-pass filtering on each high-pass filtered monoaxial acceleration signal by using the low-pass or band-pass filter;
an extreme value point obtaining unit, for obtaining acceleration signal extreme value points from each low-pass or band-pass filtered monoaxial acceleration signal and removing interfering extreme value points therein;
a counting unit, for counting the number of the acceleration signal extreme value points of each low-pass or band-pass filtered monoaxial acceleration signal after the interfering extreme value points have been removed;
a step counting unit, for determining the walkrun step number obtained from this round of step counting based on the number of the acceleration signal extreme value points in three monoaxial acceleration signals with the interfering extreme value points removed as counted by the counting unit, and calculating the accumulative walkrun step number of the walkrunner.

Preferably, the pitch detecting unit can comprise:
an attenuation filter, for performing attenuation process on each high-pass filtered monoaxial acceleration signal in such a manner that attenuation degree increases from low frequency to high frequency;

a calculating unit, for calculating an autocorrelation function $\rho(\tau)$ of the signal output from the attenuation filter by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, $a(n)$ is the n-th value of the signal, N is the predetermined length of the signal, and $0 \leq n < N$, $\tau$ is a delay time, $\rho(\tau)$ is a normalized autocorrelation function of the signal;
a pitch obtaining unit, for obtaining the value of v corresponding to the maximal value of $\rho(\tau)$, and outputting the reciprocal of the $\tau$ value as the pitch of the high-pass filtered monoaxial acceleration signal.

Preferably, the step counting unit can comprise an acceleration signal energy calculating unit, for calculating the energy of each of the monoaxial acceleration signals, and if the energy of each monoaxial acceleration signal is not markedly different, the step counting unit averages the number of the acceleration signal extreme value points, with the interfering extreme value points removed, corresponding to each axis, and takes the average number as the walkrun step number obtained in this round of step counting; or, if the energy of each monoaxial acceleration signal is markedly different, the step counting unit determines the walkrun step number obtained in this round of step counting based on the number of the acceleration signal extreme value points, with the interfering extreme value points removed, corresponding to the monoaxial acceleration signal with the largest energy.

It can be known from the above description that, the step counting method and device of the present invention can better obtain pitch component of three monoaxial acceleration signals output from the triaxial acceleration sensor by performing high-pass filtering, low-pass or band-pass filtering on these three monoaxial acceleration signals, and on such basis, can count the extreme value points corresponding to walkrun step number in the monoaxial acceleration signal more accurately by removing the interfering extreme value points, thus can perform step counting accurately, and facilitate the pedometer's wearer to monitor sports schemes accurately.

The aforesaid description is merely the summary of technical solution of the present invention, and for understanding the technical means of the present invention more clearly, it can be carried out according to the disclosure of specification, and for making the aforesaid and other objectives, features and advantages of the present invention more apparent to be understood, embodiments of the present invention are illustrated as follows.

BRIEF DESCRIPTION OF DRAWINGS

By reading the detailed description of the preferable embodiment hereinafter, all the other features and advantages will be apparent to those skilled in the art. The attached drawings are merely for the purpose of showing preferable embodiment, rather than deemed as a limitation of the present invention. Among the attached drawings.

DETAILED DESCRIPTION OF THE INVENTION

Figure 1:
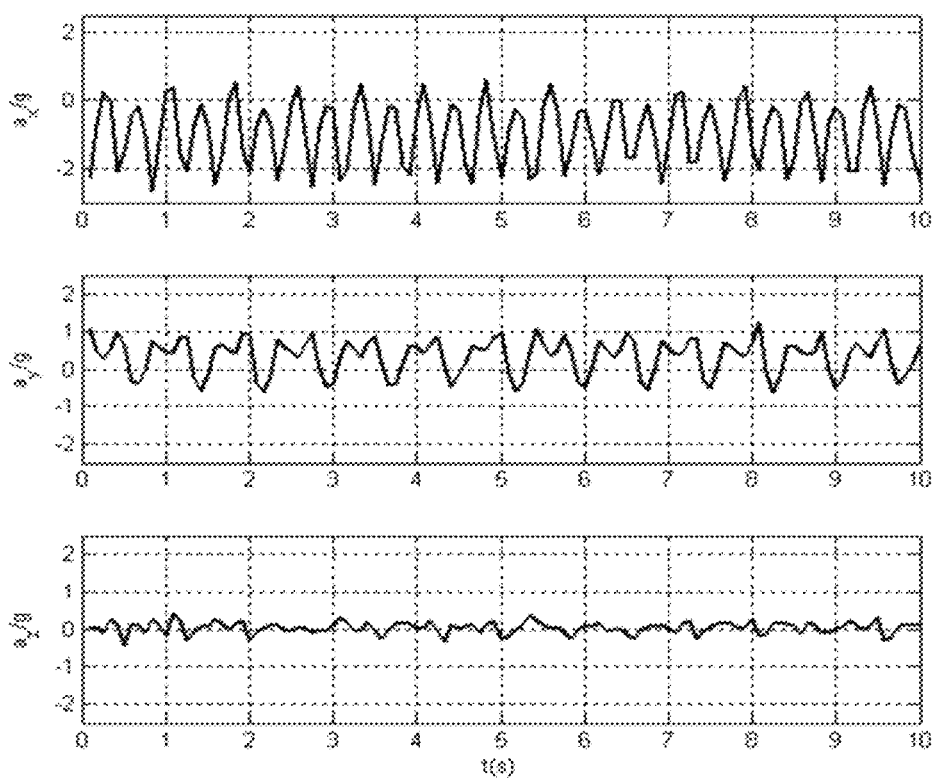
FIG. 1 is a schematic drawing, showing an example of acceleration signal produced by a triaxial acceleration sensor in three orientations during walkrun of its wearer.

The present invention will be described in details in combination with the attached drawings and specific embodiments.

In the following description, certain illustrative embodiments of the present invention are described only by illustration. Needless to say, one skilled in the art may recognize that, the embodiment can be amended by using a variety of different ways without departing from the spirit and scope of the present invention. Accordingly, the attached drawings and descriptions are illustrative in nature, and not intended to limit the protection scope of the claims. In the present specification, the same reference numerals denote the same or similar parts.

The step counting method of the present invention is suitable for step counting with a pedometer having a triaxial acceleration sensor. The pedometer having the triaxial acceleration sensor produces oscillatory acceleration signal with different magnitude values on each direction during walkrun of its wearer. FIG. 1 is a schematic drawing, showing an example of acceleration signal produced by the triaxial acceleration sensor in three directions during walkrun of its wearer, wherein, $a_x/g$, $a_y/g$, $a_z/g$ are normalized acceleration signals produced by the triaxial acceleration sensor in x axis, y axis and z axis, respectively, g denotes acceleration of gravity. As shown in FIG. 1, $a_x/g$, $a_y/g$, $a_z/g$ contain the same pitch although their magnitude values are different, and the pitch represents the reciprocal of motion period that both left foot and right foot of the pedometer's wearer move one step. In addition, $a_x/g$, $a_y/g$, $a_z/g$ contain double frequency component, which corresponds to the reciprocal of motion period that either left foot or right foot of the pedometer's wearer moves one step. In addition, the acceleration signal may further contain higher frequency component produced by other rhythmical motion of the body. Since the output of the triaxial acceleration sensor also contains high-frequency component and other noises besides the pitch component, the step counting will not be accurate if the walkrun step number is determined by directly searching the extreme value points of the acceleration signal. Therefore, the present invention provides a step counting method by processing the acceleration signal output by the triaxial acceleration sensor to accurately obtain the extreme value points corresponding to the pitch component in the acceleration signal, so as to obtain walkrun step number accurately.

Figure 2:
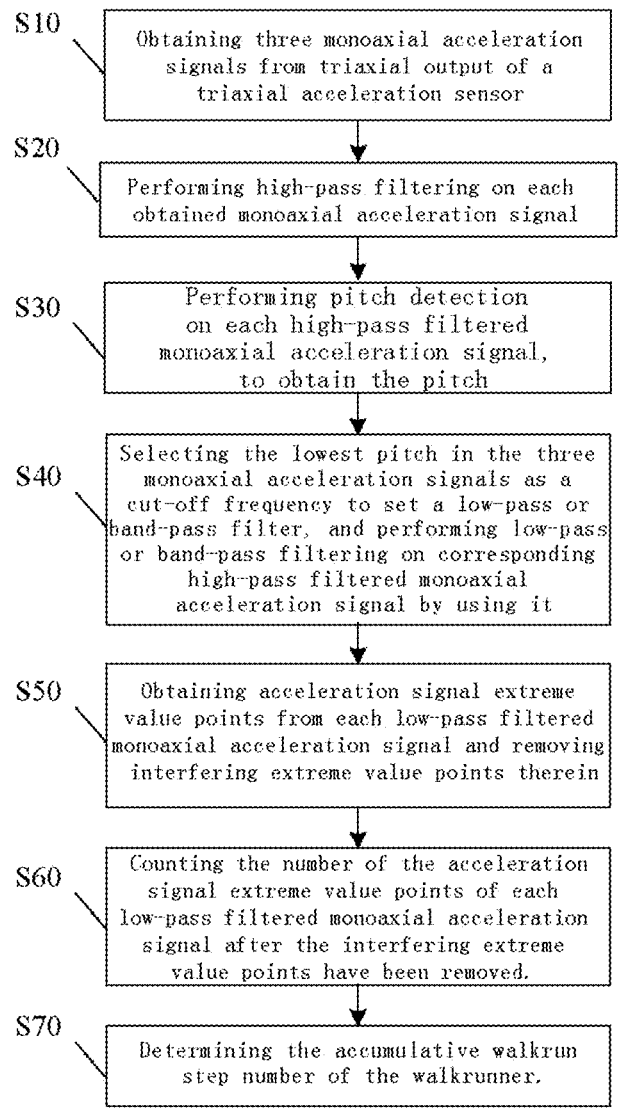
FIG. 2 is a block diagram, showing a step counting method of one embodiment of the present invention.
Figure 3A:
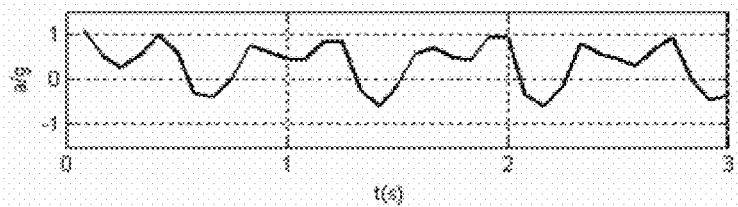
FIG. 3a is a signal graph, showing a representative normalized monoaxial acceleration signal with a predetermined length output from the triaxial acceleration sensor.

FIG. 2 is a block diagram, showing a step counting method of one embodiment of the present invention. As shown in FIG. 2, the step counting method of the embodiment of the present invention comprises the following steps:

Firstly, in step S10, obtaining three monoaxial acceleration signals with a predetermined length from triaxial output of a triaxial acceleration sensor worn on a walkrunner. FIG. 3a is a signal graph, showing the representative normalized monoaxial acceleration signal a/g having a predetermined length output from the triaxial acceleration sensor, wherein, a denotes acceleration, g denotes acceleration of gravity. The predetermined length can be chosen according to actual situation, and if the predetermined length is too long, it would not be easy to obtain walkrun step number instantly, on the other hand, if the predetermined length is too short, the accuracy of step counting would decrease. In the example of FIG. 3, the predetermined length is chosen to be 3 seconds, while the present invention is not restricted thereto.

Figure 3B:
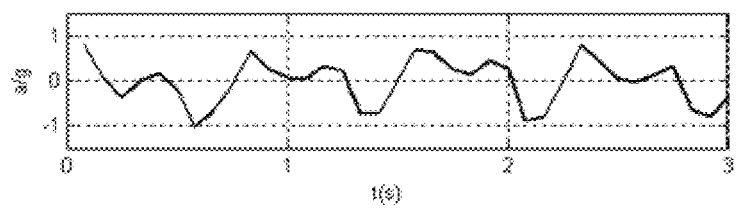
FIG. 3b is a signal graph, showing a high-pass filtered monoaxial acceleration signal.

Subsequently, in step S20, performing high-pass filtering on each obtained monoaxial acceleration signal. Since each monoaxial acceleration signal output from the triaxial acceleration sensor generally contains direct current (DC) component, and the existence of the DC component interferes with the analysis of each monoaxial acceleration signal, therefore, the DC component in the monoaxial acceleration signal is removed through high-pass filtering. FIG. 3b is a signal graph, showing a high-pass filtered monoaxial acceleration signal. It can be seen from FIG. 3b that, after high-pass filtering, the monoaxial acceleration signal only contains alternative current (AC) component.

Figure 4:
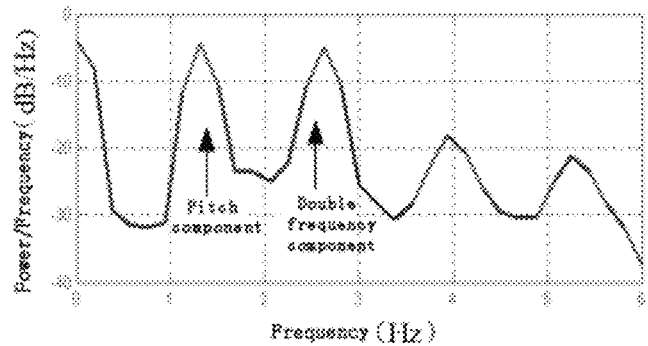
FIG. 4 is a schematic spectral diagram of monoaxial acceleration signal.

Subsequently, in step S30, performing pitch detection on each high-pass filtered monoaxial acceleration signal, to obtain the pitch of each monoaxial acceleration signal. As mentioned above, the monoaxial acceleration signal produced during walkrun may contain various frequency components corresponding to different rhythmical motions of the body, such as pitch component, double frequency component and other high-frequency component. FIG. 4 is a schematic spectral diagram of monoaxial acceleration signal. Wherein, the pitch component is closely related to walkrun step number, and it is more accurate to obtain walkrun step number based on the pitch component. In order to obtain the acceleration signal only having the pitch component, it is necessary to filter out the high-frequency components from the acceleration signal. And for filtering out the high-frequency components, it is required to detect the frequency of the pitch component roughly, to facilitate constructing a suitable filter for filtering out the high-frequency components beyond the pitch component.

There are various methods for pitch detection, e.g., conventional methods in voice signal pitch detection such as autocorrelation function method, cepstrum method, linear predictive coding method, average magnitude difference function method can be used. Preferably, autocorrelation function method can be used.

Specifically, for each high-pass filtered monoaxial acceleration signal, firstly the autocorrelation function $\rho(\tau)$ of the signal is calculated by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, a(n) is the n-th value of the signal, N is the predetermined length of the signal, and $0 \leq n < N$, $\tau$ is a delay time, $\rho(\tau)$ is a normalized autocorrelation function of the signal. Then, obtaining the value of $\tau$ corresponding to the maximal value of $\rho(\tau)$, and the reciprocal of the $\tau$ value is the pitch of the signal.

Figure 5:
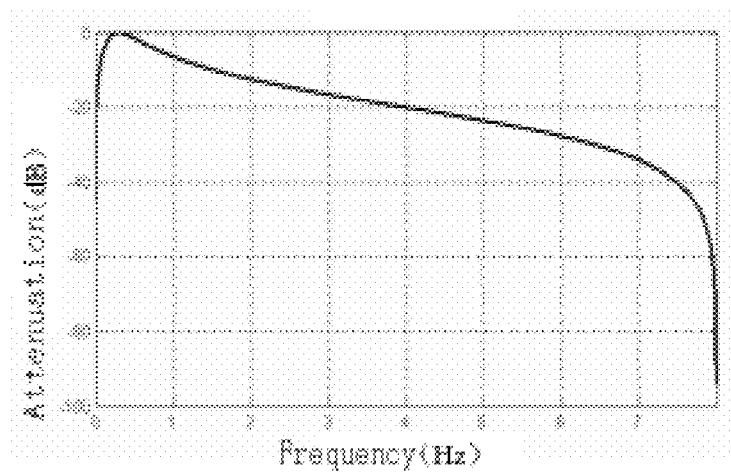
FIG. 5 shows an example of frequency response curve of a filter with which the attenuation of signal energy increases progressively from low frequency to high frequency.

In an actual monoaxial acceleration signal, other frequency components (e.g. double frequency component) besides the pitch sometimes have rather large energy, as shown in FIG. 4. Thus, when calculating the maximal value of $\rho(\tau)$ to obtain the value of $\tau$ corresponding to the maximal value, a rather big error may be produced. Therefore, in order to obtain the pitch $1/\tau$ accurately by using the autocorrelation function method, before obtaining the autocorrelation function $\rho(\tau)$, it is possible to selectively attenuate the monoaxial acceleration signal firstly, to suppress the high-frequency components in the monoaxial acceleration signal, so as to highlight the pitch component in the monoaxial acceleration signal, and reduce the error of the obtained pitch. In one embodiment of the present invention, the attenuation process on the monoaxial acceleration signal can be done by a filter with which the attenuation of signal energy increases progressively from low frequency to high frequency. FIG. 5 shows an example of frequency response curve of the filter with which the attenuation of signal energy increases progressively from low frequency to high frequency. After the monoaxial acceleration signal is attenuated through the filter, the low-frequency component in the signal is attenuated rather slightly, whereas the high-frequency component is attenuated rather greatly. Thus, when the pitch is calculated by further performing autocorrelation function method on the monoaxial acceleration signal having filtered through the filter, the obtained pitch is relatively accurate.

Figure 3C:
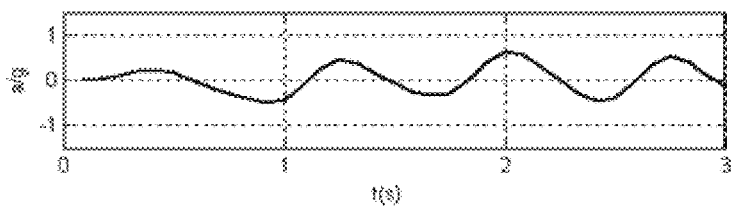
FIG. 3c is a signal graph, showing a low-pass or band-pass filtered monoaxial acceleration signal.

Subsequently, in step S40, selecting the lowest pitch in the three monoaxial acceleration signals as a cut-off frequency to set a low-pass or band-pass filter, and performing low-pass or band-pass filtering on each high-pass filtered monoaxial acceleration signal by using the low-pass or band-pass filter. After low-pass or band-pass filtering, it is possible to obtain a relatively smooth signal, so as to facilitate accurately counting the extreme value points of the acceleration signals corresponding to the walkrun step number. FIG. 3c is a signal graph, showing a low-pass or band-pass filtered monoaxial acceleration signal.

Figure 3D:
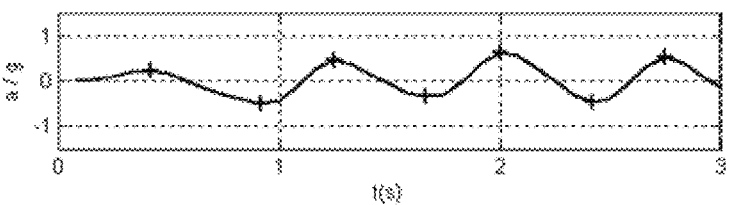
FIG. 3d is a signal graph, showing one example of extreme value point of low-pass or band-pass filtered monoaxial acceleration signal.
Figure 6:
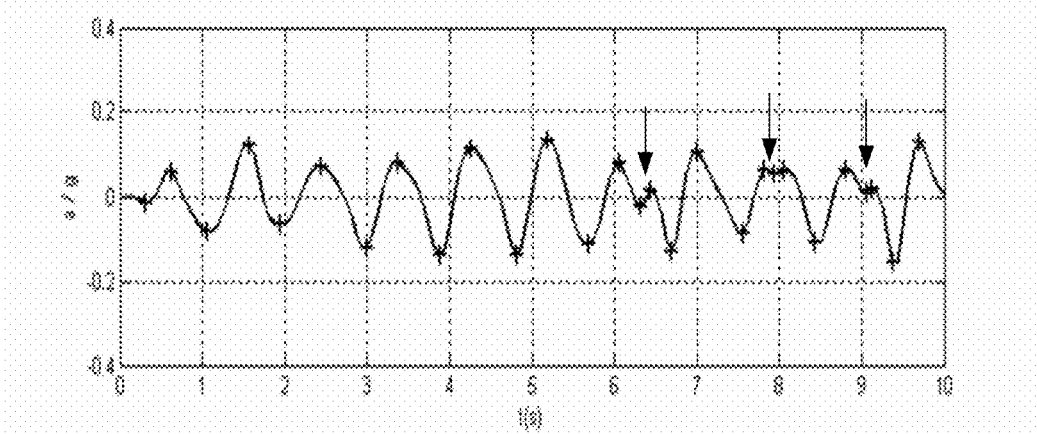
FIG. 6 is a signal graph, showing another example of extreme value point of low-pass or band-pass filtered monoaxial acceleration signal.

Subsequently, in step S50, obtaining acceleration signal extreme value points from each low-pass or band-pass filtered monoaxial acceleration signal and removing interfering extreme value points therein. FIG. 3d is a signal graph, showing one example of extreme value points of low-pass or band-pass filtered monoaxial acceleration signal, wherein, symbol+denotes the extreme value points (including maximal and minimal value points). FIG. 3d demonstrates a rather specific example, wherein, noise interference in the low-pass or band-pass filtered monoaxial acceleration signal is almost non-existent. In a more general condition, after low-pass or band-pass filtering, there still exists noise interference in the monoaxial acceleration signal, which is manifested as the existence of interfering extreme value points. FIG. 6 is a signal graph, showing another example of extreme value points of low-pass or band-pass filtered monoaxial acceleration signal. As shown in FIG. 6, interfering extreme value points (as indicated by arrow in FIG. 6) exists in the low-pass or band-pass filtered monoaxial acceleration signal, these interfering extreme value points do not represent the extreme value points related to periodic motion, which only result in over-counting of step number, and removing these interfering extreme value points can make the counted step number more accurate. Thus, these interfering extreme value points need to be removed so as to obtain the extreme value points corresponding to walkrun step number accurately.

In fact, the walkrun step number only corresponds to the number of extreme value points in the monoaxial acceleration signal, and is not closely related to the exact positions of these extreme value points, in other words, it is enough to remove appropriate number of extreme value points for ensuring that the motion period of both left foot and right foot moving one step corresponds to an extreme value point. Therefore, the method for removing interfering extreme value point may not be unique.

In one embodiment of the present invention, the interfering extreme value points may comprise such an acceleration signal extreme value point that the time gap between this acceleration signal extreme value point and the previous acceleration signal extreme value point is smaller than a predetermined threshold, wherein, the predetermined threshold is far smaller than the period of the pitch component of the monoaxial acceleration signal. In this embodiment, in each group of extreme value points positioning closer, only the leftmost extreme value point is kept, while the other extreme value points are removed as interfering extreme value points. In this manner, according to the time gap between acceleration signal extreme value points, the interfering extreme value points are filtered out from the acceleration signal extreme value points.

In another embodiment of the present invention, the interfering extreme value points may comprise acceleration signal extreme value points, whose magnitude values are not maximal, among each group of acceleration signal extreme value points in which the time gap between any two adjacent acceleration signal extreme value points is smaller than a predetermined threshold. In other words, in this embodiment, in each group of extreme value points positioning closer, only the acceleration signal extreme value point with maximal magnitude value is kept, while the other extreme value points are removed as interfering extreme value points. In this manner, according to the time gap between acceleration signal extreme value points and the magnitude values of acceleration signal extreme value points, the interfering extreme value points are filtered out from the acceleration signal extreme value points.

Subsequently, in step S60, counting the number of the acceleration signal extreme value points of each low-pass or band-pass filtered monoaxial acceleration signal after the interfering extreme value points have been removed.

Subsequently, in step S70, determining the walkrun step number obtained from this round of step counting based on the number of the acceleration signal extreme value points in three monoaxial acceleration signals with the interfering extreme value points removed as counted in step S60, and calculating the accumulative walkrun step number of the walkrunner.

For example, if the energy of each monoaxial acceleration signal is not markedly different (it can be determined whether the energy is not markedly different by setting a predetermined threshold), average the number of the acceleration signal extreme value points, with the interfering extreme value points removed, corresponding to each axis, and the average number is taken as the walkrun step number obtained in this round of step counting. For another example, if the energy of each monoaxial acceleration signal is markedly different (it can be determined whether the energy is markedly different by setting a predetermined threshold), the walkrun step number obtained in this round of step counting can be determined based on the number of the acceleration signal extreme value points, with the interfering extreme value points removed, corresponding to the monoaxial acceleration signal with the largest energy.

Repeating the aforesaid steps S10-S70, the walkrun step number obtained in each round of step counting is accumulated, thus a total accumulative step number can be obtained.

In addition, in the aforesaid method, a displacement can be calculated based on quadratic integral of at least one monoaxial acceleration signal for time, so as to provide a reference of actual motion distance for the walkrunner. In addition, motion in situ or actual walkrun can be distinguished according to the size of the displacement.

Hereinbefore the step counting method of the present invention is described with reference to FIGS. 1-6. The step counting method of the present invention can be achieved through software, and can also be achieved through hardware, or achieved in combination with software and hardware.

Figure 7:
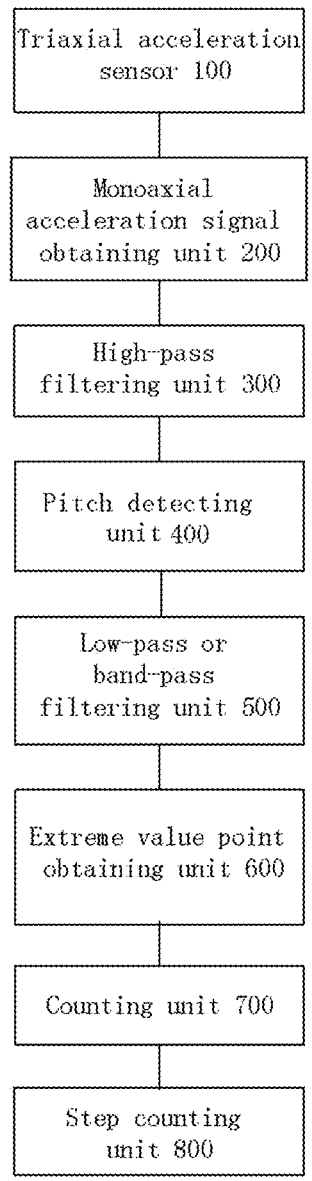
FIG. 7 is a block diagram, showing a step counting device of one embodiment of the present invention.

FIG. 7 is a block diagram, showing a step counting device of one embodiment of the present invention. As shown in FIG. 7, the step counting device 1000 comprises: a triaxial acceleration sensor 100, a monoaxial acceleration signal obtaining unit 200, a high-pass filtering unit 300, a pitch detecting unit 400, a low-pass or band-pass filtering unit 500, an extreme value point obtaining unit 600, a counting unit 700, and a step counting unit 800.

The monoaxial acceleration signal obtaining unit 200 is for obtaining three monoaxial acceleration signals with a predetermined length from the triaxial output of the triaxial acceleration sensor 100 worn on a walkrunner.

The high-pass filtering unit 300 is for performing high-pass filtering on each monoaxial acceleration signal obtained from the monoaxial acceleration signal obtaining unit 200.

The pitch detecting unit 400 is for performing pitch detection on each high-pass filtered monoaxial acceleration signal to obtain the pitch of each monoaxial acceleration signal.

The low-pass or band-pass filtering unit 500 selects the lowest pitch of the three monoaxial acceleration signals as a cut-off frequency to set a low-pass or band-pass filter, and performs low-pass or band-pass filtering on each high-pass filtered monoaxial acceleration signal by using the low-pass or band-pass filter.

The extreme value point obtaining unit 600 is for obtaining acceleration signal extreme value points from each low-pass or band-pass filtered monoaxial acceleration signal and removing interfering extreme value points therein.

The counting unit 700 is for counting the number of the acceleration signal extreme value points of each low-pass or band-pass filtered monoaxial acceleration signal after interfering extreme value points have been removed.

The step counting unit 800 determines the walkrun step number obtained from this round of step counting based on the number of the acceleration signal extreme value points in three monoaxial acceleration signals with the interfering extreme value points removed as counted by the counting unit 700, and calculates the accumulative walkrun step number of the walkrunner.

Preferably, the pitch detecting unit 400 can comprise: an attenuation filter, for performing attenuation process on each high-pass filtered monoaxial acceleration signal in such a manner that attenuation degree increases progressively from low frequency to high frequency; a calculating unit, for calculating an autocorrelation function $\rho(\tau)$ of the signal output from the attenuation filter by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, a(n) is the n-th value of the signal, N is the predetermined length of the signal, and $0 \le n < N$, $\tau$ is a delay time, $\rho(\tau)$ is a normalized autocorrelation function of the signal; a pitch obtaining unit, for obtaining the value of $\tau$ corresponding to the maximal value of $\rho(\tau)$, and outputting the reciprocal of the $\tau$ value as the pitch of the high-pass filtered monoaxial acceleration signal.

Preferably, the step counting unit 800 can comprise an acceleration signal energy calculating unit, for calculating the energy of each of the monoaxial acceleration signals, and if the energy of each monoaxial acceleration signal is not markedly different, the step counting unit 800 averages the number of the acceleration signal extreme value points, with the interfering extreme value points removed, corresponding to each axis, and takes the average number as the walkrun step number obtained in this round of step counting; or, if the energy of each monoaxial acceleration signal is markedly different, the step counting unit 800 determines the walkrun step number obtained in this round of step counting based on the number of the acceleration signal extreme value points, with the interfering extreme value points removed, corresponding to the monoaxial acceleration signal with the largest energy.

Hereinbefore the step counting method and device according to the present invention are described with reference to the attached drawings in an illustrative way. However, those skilled in the art should understand that, regarding the aforesaid step counting method and device in the present invention, various modification can be made without departing from the content of the present invention. Hence, the protection scope of the present invention should be determined by the content of appended claims.

It should be noted that:

Each component in the present invention can be achieved by hardware, or achieved by the software modules run on one or more processors, or achieved in a combination thereof. Those skilled in the art should understand that, some or all functions of some or all components according to the embodiments of the present invention can be achieved by using micro-processor or digital signal processor (DSP) in practice. The present invention can also be implemented as equipment or device program for carrying out part or all of the described method herein (for example, computer program and computer program product). The program implementing the present invention as such can be stored on a computer readable medium, or may be in a form of one or more signals. Such a signal can be downloaded from internet website, or provided on a carrier signal, or provided in any other forms.

Figure 8:
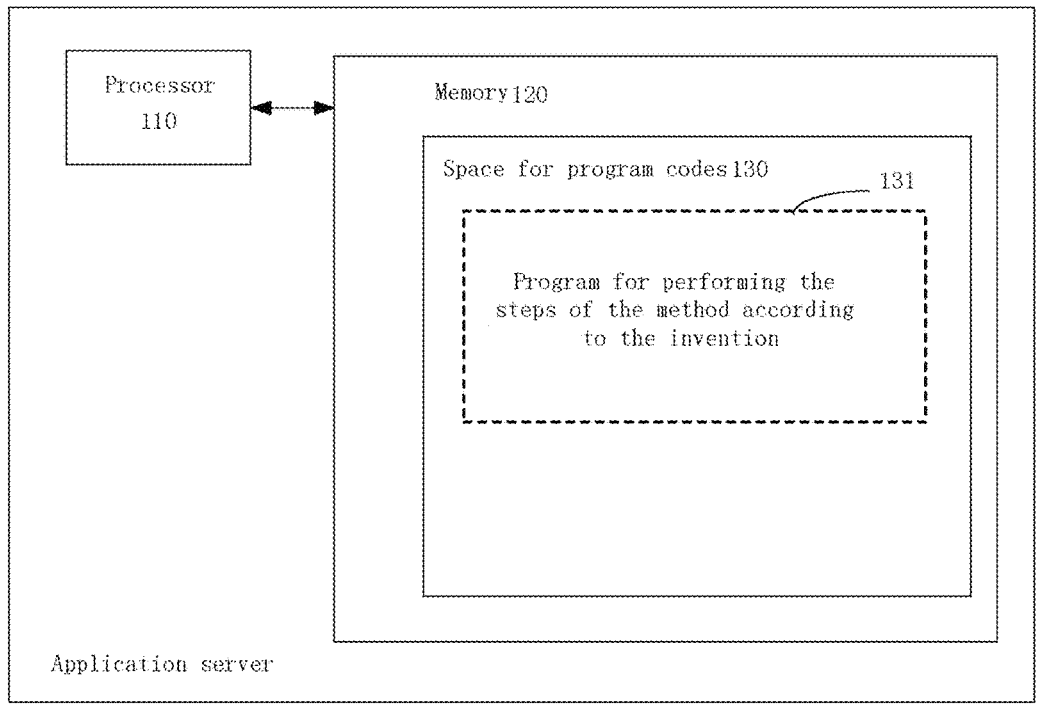
FIG. 8 schematically shows a block diagram of server for carrying out the method according to the present invention.
Figure 9:
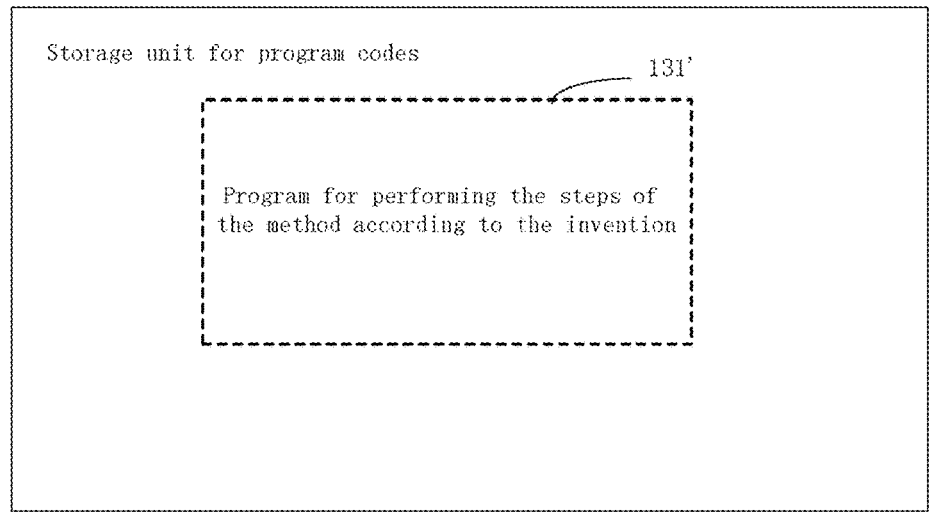
FIG. 9 schematically shows a storage unit for maintaining or carrying the program codes for achieving the method according to the present invention.

For example, FIG. 8 shows a server capable of implementing the step counting method according to the present invention, e.g., an application server. The server traditionally comprises a processor 110 and a computer program product or computer readable medium in a form of memory 120. The memory 120 can be electronic memory, such as flash memory, EEPROM (electrically erasable programmable read only memory), EPROM, hard disk, ROM or the like. The memory 120 has storage space 130 for the program codes 131 for performing the steps of any method in the aforesaid methods. For example, the storage space 130 for the program codes can comprise program codes 131 respectively for implementing each step in the aforesaid methods. These program codes can be read/written from/into one or more computer program products. These computer program products comprise program code carriers such as hard disk, compact disk (CD), memory card or floppy disk and the like. Such a computer program product is generally a portable or fixed storage unit as shown in FIG. 9. The storage unit may have storage segments, storage space and the like similar to the memory 120 in the server of FIG. 8. The program codes can be compressed in a suitable form. Generally, the storage unit comprises computer readable codes 131' for implementing the steps of the method according to the present invention, i.e., codes that can be read by a processor such as 110, and when these codes are run by a server, each step in the aforesaid described method is carried out on the server.

It should be noted that the aforesaid embodiments are for explaining the present invention rather than limiting the present invention, and those skilled in the art can design alternative embodiments without departing from the scope of appended claims. In the claims, any reference symbol located between parentheses should not be construed as limitation to the claims. Word "comprising" does not exclude the existence of element or step not listed in the claims. The present invention can be implemented through hardware comprising various different elements and through suitably programmed computer. In the product claim listing various devices, some of these devices can be specifically implemented by one hardware item.

In the description provided herein, numerous specific details are described. However, it can be understood that, the embodiments of the present invention can be carried out without these specific details. In some embodiments, well-known methods, structures and techniques are not described in details, so as not to blur the understanding to the present specification. The terms used in the present specification are mainly selected for the purpose of readability and teaching, rather than selected for explaining or limiting the subject matter of the present invention.

What is claimed is:

1. A step counting method, wherein the step counting method is performed by using an electronic step counting device worn on a walk runner and comprising a triaxial acceleration sensor, a memory having instructions stored thereon and at least one processor, the method comprises the following steps performed by the at least one processor based on instructions stored on the memory:

obtaining three monoaxial acceleration signals with a predetermined length from triaxial output of the triaxial acceleration sensor;
performing high-pass filtering on each obtained monoaxial acceleration signal;
performing pitch detection on each high-pass filtered monoaxial acceleration signal, to obtain a pitch of each monoaxial acceleration signal;
selecting a lowest pitch in the three monoaxial acceleration signals as a cut-off frequency to set a low-pass or band-pass filter, and performing low-pass or band-pass filtering on each high-pass filtered monoaxial acceleration signal by using the low-pass or band-pass filter;
obtaining acceleration signal extreme value points from each low-pass or band-pass filtered monoaxial acceleration signal and removing interfering extreme value points from the acceleration signal extreme value points;
counting a number of the acceleration signal extreme value points of each low-pass or band-pass filtered monoaxial acceleration signal after the interfering extreme value points have been removed;
determining a walkrun step number obtained from around of step counting based on a result of counting, and calculating an accumulative walkrun step number of the walkrunner.

2. The step counting method according to claim 1, wherein, one or more methods of autocorrelation function method, cepstrum method, linear predictive coding method, and average magnitude difference function method are used in the pitch detection.

3. The step counting method according to claim 2, wherein, the performing pitch detection on each high-pass filtered monoaxial acceleration signal comprises:

performing attenuation process on each high-pass filtered monoaxial acceleration signal by using a filter with which the attenuation of signal energy increases from low frequency to high frequency;
calculating an autocorrelation function $\rho(\tau)$ of each high-pass filtered monoaxial acceleration signal after the attenuation process by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, a(n) is the n-th value of each high-pass filtered monoaxial acceleration signal, N is the predetermined length of each high-pass filtered monoaxial acceleration signal, and $0 \leq n < N$, $\tau$ is a delay time, $\rho(\tau)$ is a normalized autocorrelation function of the signal;
obtaining the value of $\tau$ corresponding to the maximal value of $\rho(\tau)$, and the reciprocal of the $\tau$ value is the pitch of each high-pass filtered monoaxial acceleration signal.

4. The step counting method according to claim 1, wherein, the removing the interfering extreme value points from the acceleration signal extreme value points comprises:

filtering out the interfering extreme value points from the acceleration signal extreme value points through time gap; or, filtering out the interfering extreme value points from the acceleration signal extreme value points through time gap and magnitude value.

5. The step counting method according to claim 4, wherein, the interfering extreme value point comprises such an acceleration signal extreme value point that a time gap between the acceleration signal extreme value point and its previous acceleration signal extreme value point is smaller than a predetermined threshold.

6. The step counting method according to claim 4, wherein, the interfering extreme value points comprise acceleration signal extreme value points, whose magnitude values are not maximal, among the acceleration signal extreme value points in which a time gap between any two adjacent acceleration signal extreme value points is smaller than a predetermined threshold.

7. The step counting method according to claim 1, wherein, the determining a walkrun step number obtained from a round of step counting based on a result of counting comprises:
if energy difference of each monoaxial acceleration signal is less than a predetermined threshold, averaging numbers of the acceleration signal extreme value points corresponding to each monoaxis after the interfering extreme value points have been removed, and taking an average number as the walkrun step number obtained in this round of step counting;
or, if energy difference of each monoaxial acceleration signal is larger than the predetermined threshold, determining the walkrun step number obtained in this round of step counting based on the number of the acceleration signal extreme value points corresponding to a monoaxial acceleration signal with highest energy after the interfering extreme value points have been removed.

8. The step counting method according to claim 1, further comprises: calculating displacement based on quadratic integral of at least one monoaxial acceleration signal for time.

9. A computer program, comprising program readable codes, when the program readable codes are operated on a server, the server implements the step counting method according to claim 1.

10. A computer readable medium, for storing the computer program according to claim 9.

11. An electronic step counting device, wherein the electric step counting device is worn on a walkrunner and comprises a triaxial acceleration sensor, a memory having instructions stored thereon and at least one processor, the at least one processor performs the following operations based on instructions stored on the memory:
obtaining three monoaxial acceleration signals with a predetermined length from a triaxial output of the triaxial acceleration sensor;
performing high-pass filtering on each monoaxial acceleration signal obtained;
performing pitch detection on each high-pass filtered monoaxial acceleration signal to obtain a pitch of each monoaxial acceleration signal;
selecting a lowest pitch in the three monoaxial acceleration signals as a cut-off frequency to set a low-pass or band-pass filter, and performing low-pass or band-pass filtering on each high-pass filtered monoaxial acceleration signal by using the low-pass or band-pass filter;
obtaining acceleration signal extreme value points from each low-pass or band-pass filtered monoaxial acceleration signal and removing interfering extreme value points therein;
counting a number of the acceleration signal extreme value points of each low-pass or band-pass filtered monoaxial acceleration signal after the interfering extreme value points have been removed;
determining a walkrun step number obtained from a round of step counting based on the result counted, and calculating an accumulative walkrun step number of the walkrunner.

12. The step counting device according to claim 11, wherein, the operation of performing pitch detection on each high-pass filtered monoaxial acceleration signal to obtain a pitch of each monoaxial acceleration signal comprises:
performing attenuation process on each high-pass filtered monoaxial acceleration signal in such a manner that attenuation of signal energy increases from low frequency to high frequency;
calculating an autocorrelation function $\rho(\tau)$ of a signal output from the attenuation filter by using the following formula:

$$\rho(\tau) = \frac{\sum_{n=0}^{N-1} a(n)a(n-\tau)}{\sqrt{\sum_{n=0}^{N-1} a^2(n) \sum_{n=0}^{N-1} a^2(n-\tau)}}$$

wherein, a(n) is the n-th value of each high-pass filtered monoaxial acceleration signal, N is the predetermined length of each high-pass filtered monoaxial acceleration signal, and $0 \le n < N$, $\tau$ is a delay time, $\rho(\tau)$ is a normalized autocorrelation function of each high-pass filtered monoaxial acceleration signal;
obtaining the value of $\tau$ corresponding to the maximal value of $\rho(\tau)$, and outputting the reciprocal of the $\tau$ value as a pitch of the high-pass filtered monoaxial acceleration signal.

13. The step counting device according to claim 11, wherein, the operation of determining a walkrun step number obtained from a round of step counting based on the result counted, and calculating an accumulative walkrun step number of the walkrunner comprises:
calculate energy of each monoaxial acceleration signal, and
if energy difference of each monoaxial acceleration signal is less than a predetermined threshold, averaging numbers of the acceleration signal extreme value points corresponding to each monoaxis after the interfering extreme value points have been removed, and taking an average number as the walkrun step number obtained in a around of step counting;
or, if energy difference of each monoaxial acceleration signal is larger than the predetermined threshold, determining the walkrun step number obtained in the round of step counting based on the number of the acceleration signal extreme value points corresponding to a monoaxial acceleration signal with highest energy after the interfering extreme value points have been removed.

* * * * *